(12) United States Patent
Pruter

(10) Patent No.: US 8,353,840 B1
(45) Date of Patent: Jan. 15, 2013

(54) METHOD AND DISPOSABLE APPARATUS FOR GUIDING NEEDLES WITH A DOUBLE BUTTON UNLOCKING AND LOCKING MECHANISM

(76) Inventor: Rick L. Pruter, Iowa City, IA (US)

( * ) Notice: Subject to any disclaimer, the term of this patent is extended or adjusted under 35 U.S.C. 154(b) by 3436 days.

(21) Appl. No.: 10/707,815

(22) Filed: Jan. 14, 2004

Related U.S. Application Data

(63) Continuation-in-part of application No. 10/065,029, filed on Sep. 11, 2002, now Pat. No. 6,758,817.

(51) Int. Cl.
 *A61B 8/14* (2006.01)
(52) U.S. Cl. .......... 600/464; 24/327; 600/459; 600/461; 604/174
(58) Field of Classification Search ............ 604/113, 604/116, 174, 178, 240, 242, 243; 600/459, 600/461, 464; 606/130; 24/327, 330, 494, 24/517, 527, 538, 543, 544; 128/DIG. 26
See application file for complete search history.

(56) References Cited

U.S. PATENT DOCUMENTS

| | | |
|---|---|---|
| 2,451,183 A | 6/1947 | Tantimonaco |
| 2,536,963 A | 1/1951 | Stephens |
| 3,017,887 A | 1/1962 | Heyer |
| 3,538,915 A | 11/1970 | Frampton et al. |
| 3,556,079 A | 1/1971 | Omizo |
| 4,029,084 A | 6/1977 | Soldner |
| 4,058,114 A | 11/1977 | Soldner |
| 4,108,165 A | 8/1978 | Kopp et al. |
| 4,132,496 A | 1/1979 | Casto |
| 4,249,539 A | 2/1981 | Vilkomerson et al. |
| 4,289,139 A | 9/1981 | Enjoji et al. |
| 4,332,248 A | 6/1982 | DeVitis |
| 4,363,326 A | 12/1982 | Kopel |
| 4,402,324 A | 9/1983 | Lindgren et al. |
| 4,408,611 A | 10/1983 | Enjoji |
| 4,469,106 A | 9/1984 | Harui |
| 4,489,730 A | 12/1984 | Jingu |
| 4,491,137 A | 1/1985 | Jingu |
| 4,497,325 A | 2/1985 | Wedel |
| 4,504,269 A | 3/1985 | Durand |
| 4,542,747 A | 9/1985 | Zurinski et al. |
| 4,635,644 A | 1/1987 | Yagata |
| 4,742,829 A | 5/1988 | Law et al. |
| 4,781,067 A | 11/1988 | Cichanski |
| 4,898,178 A | 2/1990 | Wedel |

(Continued)

FOREIGN PATENT DOCUMENTS
WO WO 99/34735 7/1999

OTHER PUBLICATIONS

"US-Guide, Free-hand Guidance for Ultrasound Interventions" brochure from UltraGuide Smart Guidance Solutions.

(Continued)

*Primary Examiner* — Kevin C Sirmons
*Assistant Examiner* — Emily Schmidt
(74) *Attorney, Agent, or Firm* — Simmons Perrine Moyer Bergman PLC

(57) ABSTRACT

An apparatus and method for guiding a needle in which the apparatus comprises a locking button for coupling the needle guide to a transceiver bracket and an unlocking button for unlatching the locking button from a coupling position, where both buttons are pushed in the same direction to accomplish their respective locking and unlatching.

10 Claims, 9 Drawing Sheets

U.S. PATENT DOCUMENTS

| | | | |
|---|---|---|---|
| 4,899,756 | A | 2/1990 | Sonek |
| 4,970,907 | A | 11/1990 | Flynn |
| 5,052,396 | A | 10/1991 | Wedel et al. |
| 5,076,279 | A | 12/1991 | Arenson et al. |
| 5,088,500 | A | 2/1992 | Wedel et al. |
| 5,161,764 | A | 11/1992 | Roney |
| 5,235,987 | A | 8/1993 | Wolfe |
| 5,343,865 | A | 9/1994 | Gardineer et al. |
| D362,064 | S | 9/1995 | Smick |
| 5,623,931 | A | 4/1997 | Wung et al. |
| D383,968 | S | 9/1997 | Bidwell et al. |
| 5,758,650 | A | 6/1998 | Miller et al. |
| 5,871,448 | A | 2/1999 | Ellard |
| 5,910,113 | A | 6/1999 | Pruter |
| 5,924,992 | A | 7/1999 | Park et al. |
| 5,941,889 | A | 8/1999 | Cermak |
| D424,693 | S | 5/2000 | Pruter |
| 6,139,544 | A | 10/2000 | Mikus |
| 6,203,499 | B1 | 3/2001 | Imling et al. |
| 6,296,614 | B1 | 10/2001 | Pruter |
| 6,311,084 | B1 | 10/2001 | Cormack et al. |
| 2001/0034530 | A1 | 10/2001 | Malackowski et al. |
| 2003/0171681 | A1* | 9/2003 | Weilandt .................. 600/464 |

OTHER PUBLICATIONS

"Dedicated Breast Ultrasound, USI Introduces a Revolution in Breast Ultrasound . . . Vista" by USI The Breast Imaging Company.

Program for Medical Ultrasound Professionals, Winter 1995, Civco Medical Instrument Co., Inc., Medical Parkway, 102 Highway 1 South, Kalona, IA 52247.

"Ultra-Pro™ Sterile General Purpose Biopsy Needle Guide". CIVCO Medical Instruments Co., Medical Parkway, 102 Highway 1 South, Kalona, IA 52247.

Solutions for Ultrasound, Civco Medical Instruments Co., Inc., Medical Parkway, 102 Highway 1 South, Kalona, IA 52247.

"Hitting the Mark with Realtime Guidance", Civco PROgram, Drawer Q, Kalona, IA 52247.

"ultrasoundsupplies.com" brochure of Civco Medical Instruments Co.

"General Purpose Needle Guides and Transducer Covers" brochure of Civco Medical Instruments, Sonosite Cross-Reference Information.

"Needle Guidance Systems, Transducer Covers, GE Medical Systems", gemedicalsystems.com brochure of Civco Medical Instruments, Solutions for Imaging.

UltraGuide 1000 System 4-page brochure, UltraGuide Ltd., Tirat Hacarmel Industrial Park, P 0 Box 2070, Tirat Hacarmel 30200, Israel.

UltraGuide 1000 2-page brochure, UltraGuide Ltd., Tirat Hacarmel Industrial Park, P O Box 2070, Tirat Hacarmel 30200, Israel.

Three-page web page of amedic.se printed on Nov. 5, 2002.

Disposable Transrectal Needle Guide, Civco Medical Instruments Co., Inc., Medical Parkway, 102 Highway 1 South, Kalona, IA 52247.

Maggi & Maggi II Plus, Sterile General Purpose Biopsy Needle Guides, Civco Medical Instrument Co., Inc., Medical Parkway, 102 Highway 1 South, Kalona, IA 52247.

Aloka Needle Guide/Probe Cover Kits, Civco Medical Instruments Co., Inc., Medical Parkway, 102 Highway 1 South, Kalona, IA 52247.

Multi Pro 2000, Multi-Purpose Ultrasound Linear Tracking Instrument, Civco Medical Instruments Co., Inc., 418 B Avenue, Kalona, IA 52247.

"Endocavity Needle Guide Kits" brochure of Civco Medical Instruments, © 2000, Solutions for Imaging.

"Civcoscan, Product News and Special Offers From Civco" Brochure of Civco Medical Instruments, Winter 2001.

* cited by examiner

METHOD AND DISPOSABLE APPARATUS FOR GUIDING NEEDLES WITH A DOUBLE BUTTON UNLOCKING AND LOCKING MECHANISM

CROSS REFERENCE TO RELATED APPLICATIONS

This application is a continuation-in-part application of an application filed on Sep. 11, 2002, having Ser. No. 10/065,029 and entitled METHOD AND DISPOSABLE APPARATUS FOR GUIDING NEEDLES. This application is incorporated herein in its entirety by this reference.

BACKGROUND OF INVENTION

In recent years, handheld medical imaging transceivers, such as ultrasound and gamma ray transceivers, have been used extensively for various medical imaging situations.

In the past, the physician or medical professional typically will cover an ultrasound transceiver with a sterile sheath. Usually, under the sheath is a mounting bracket attached to the transceiver. A needle guide is then typically attached over the sheath and coupled to the underlying bracket.

While these needle guides have been used extensively in the past, they do have some drawbacks. First of all, these needle guides require considerable attention and handto-eye coordination to be properly used. Additionally, these types of needle guides are often relatively expensive.

Consequently, there exists a need for improved methods and apparatus for guiding needles in an efficient manner.

SUMMARY OF INVENTION

It is an object of the present invention to provide an apparatus and method for guiding a needle in an efficient manner.

It is a feature of the present invention to include a plastic spring-like member.

It is another feature of the present invention to include, on the front side of the needle path, an enlarged base for guiding a needle into a grasping mechanism.

It is another feature of the present invention to include an enlarged base on a back side of the needle path for protecting the sheath from puncture by the moving needle.

It is another feature of the present invention to include a base-to-bracket attachment mechanism which is adapted for positive attachment to the bracket with a predetermined grasping force in a non-reusable manner.

It is an advantage of the present invention to achieve improved efficiency in guiding needles.

It is yet another feature of the present invention to include a double push-button locking and unlocking mechanism.

It is yet another advantage of the present invention to provide for the ability to unlock the needle guide while maintaining a force thereon which positions the needle guide in place.

The present invention is an apparatus and method for guiding needles designed to satisfy the aforementioned needs, provide the previously stated objects, include the above-listed features, and achieve the already articulated advantages. The present invention is carried out in a "surprise detachment-less" manner in a sense that the surprise or startling detachment of the needle guide from it affixed location, has been greatly reduced. Additionally, the system is carried out in a two-step manner in that the force used to unlock a needle guide is separate and distinct from the force used to remove the needle guide.

Accordingly, the present invention is an apparatus and method including a needle guide with a double push-button locking and unlocking mechanism.

BRIEF DESCRIPTION OF DRAWINGS

The invention may be more fully understood by reading the following description of the preferred embodiments of the invention, in conjunction with the appended drawings wherein.

DETAILED DESCRIPTION

Figure 1:
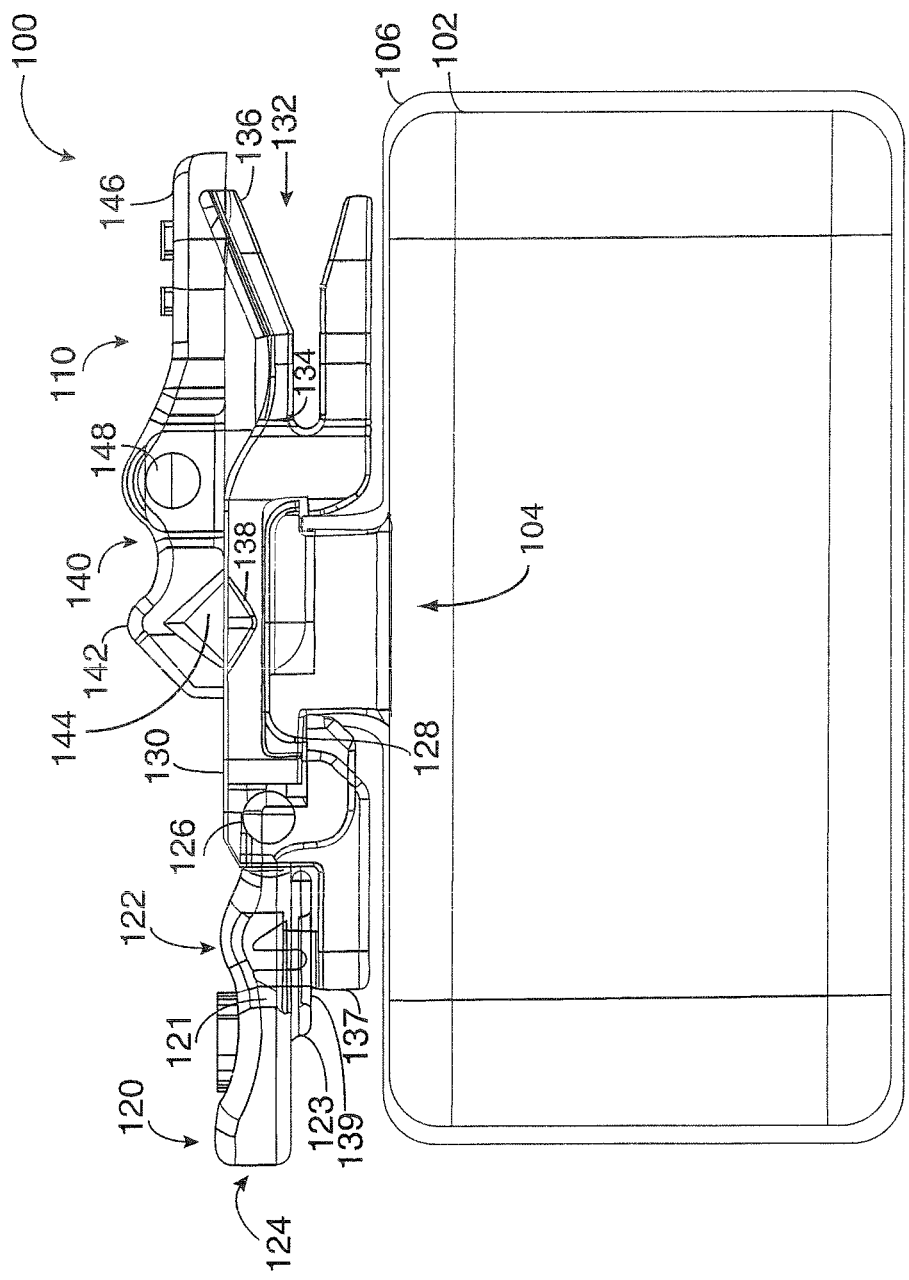
FIG. 1 is a partial cut-away side view of the apparatus of the present invention in a closed orientation.

Now referring to the drawings wherein like numerals refer to like matter throughout, and more specifically referring to FIG. 1, there is shown a needle guide, bracket and medical imaging transceiver system of the present invention, generally designated 100. The system 100 includes a medical imaging transceiver 102, which could be any type of imaging system or device, and a transceiver bracket 104, which is coupled to said medical imaging transceiver 102 for the purpose of facilitating coupling with needle guides and other instruments. Transceiver bracket 104 can be coupled to medical imaging transceiver 102 in any suitable manner, such as clamps, screws, adhesive, etc. Transceiver/bracket covering sterile sheath 106 is disposed about transceiver bracket 104 and medical imaging transceiver 102 in a well-known manner. While it has been well known in the industry to use a sterile sheath, it should be understood that it is not always necessary to use a sterile sheath in conjunction with any of the apparatuses of the present invention or in any method of the present invention. In many procedures, it may be preferred to use a sterile sheath, but it is at least conceivable that from an economic standpoint, there may be applications where not incurring the cost of a sterile sheath may be preferred. Needle guide assembly 110 is shown having a movable base portion 120, stationary base portion 130, and a needle-grasping member 140, all of which could be made of any suitable material; however, a plastic material is preferred.

Movable base portion 120 includes a bullet-nose receiving hole 122 therein which, when viewed through the cut-away portion outlined by cut-away line 121, includes a bullet-nose removal inhibitor surface 123. Movable base portion 120 also includes a movable base handle end 124 which pivots about movable base pivot point 126. On an opposing end from movable base handle end 124, is movable base bracket grasping surface 128, which is configured to grasp a surface of transceiver bracket 104 when movable base handle end 124 is disposed in a closed and locked orientation.

Needle guide assembly 110 includes stationary base portion 130, which includes a stationary base-biasing portion 132, which has a stationary base bracket mating portion 134 and a stationary base spring biasing member 136. Stationary base spring biasing member 136 is configured to provide a biasing force on needle-grasping member 140. Stationary base portion 130 further includes a stationary lock end 137 having a bullet-nose lock male member 139. Bullet-nose lock male member 139 is well known in the art for providing positive attachment between items in a manner that separation of the items results in a destruction of the future capability of the bullet-nose lock male member 139 to firmly attach the items, which mates with bullet-nose removal inhibitor surface 123 of bullet-nose receiving hole 122 in movable base portion 120. Stationary base portion 130 further includes a stationary base needle entrance-guiding channel 138 disposed along an outside top edge of stationary base portion 130.

Disposed above stationary base portion 130 is needle-grasping member 140, which has a needle-grasping end 142 with a needle receiving void 144 therein disposed in axial alignment with stationary base needle entrance-guiding channel 138, so that a needle can be simultaneously in both stationary base needle entrance-guiding channel 138 and needle receiving void 144. Needle-grasping member 140 includes a needle-grasping member handle end 146, which when depressed toward stationary base biasing portion 132, causes needle-grasping end 142 to pivot about needle-grasping member pivot point 148. Stationary base spring biasing member 136 provides a resisting force upon needle-grasping member handle end 146, which urges needle-grasping end 142 into contact with stationary base portion 130.

Figure 2:
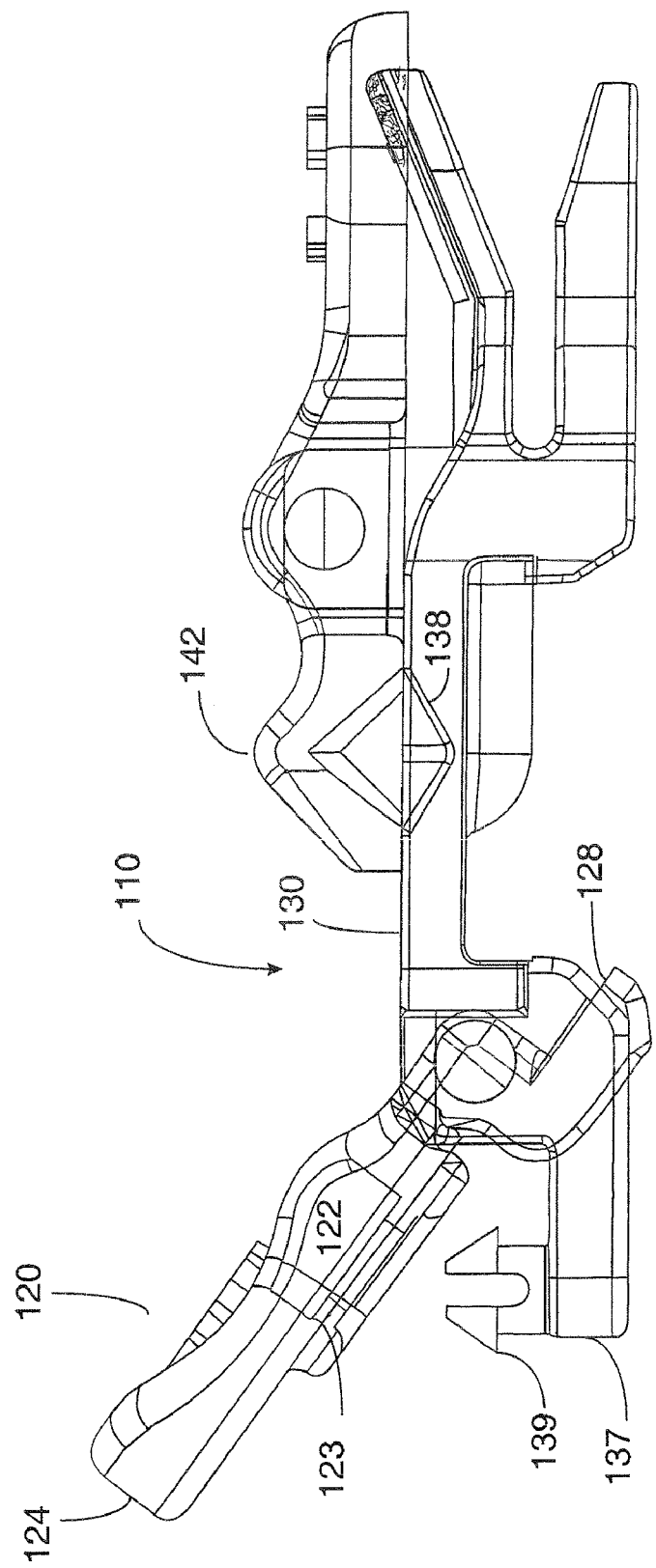
FIG. 2 is a side view of the needle guide of FIG. 1 in an open orientation prior to closing.

Now referring to FIG. 2, there is shown needle guide assembly 110 of FIG. 1 wherein movable base portion 120 is oriented in an open position prior to being closed and locked.

Figure 3:
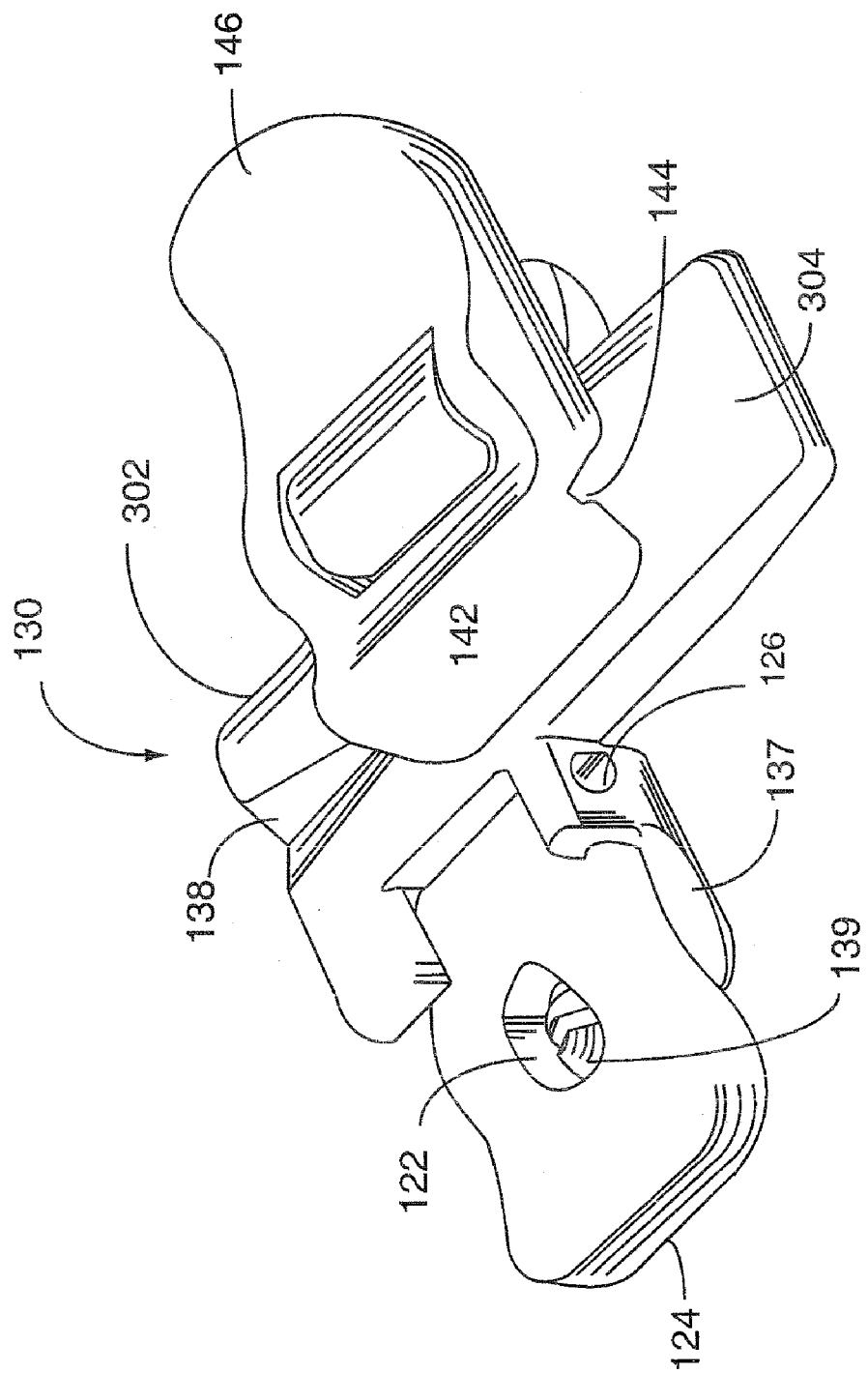
FIG. 3 is a perspective view of a needle guide of FIG. 2, which has a top enlarged sheath puncture-protecting area and a bottom enlarged sheath puncture-protecting area.

Now referring to FIG. 3, there is shown a perspective view of the needle guide assembly 110 of FIG. 2. Stationary base portion 130 is shown having a top enlarged sheath puncture-protecting area 302 and a bottom enlarged sheath puncture-protecting area 304. Top enlarged sheath puncture-protecting area 302 and bottom enlarged sheath puncture-protecting area 304 may be optional features, depending upon the particular needs of a particular application. Since the transceiver/bracket covering sterile sheath 106 (FIG. 1) is disposed adjacent to stationary base portion 130, the top enlarged sheath puncture-protecting area 302 and the bottom enlarged sheath puncture-protecting area 304 perform the functions of shielding transceiver/bracket covering sterile sheath 106 from puncture at a location of transceiver/bracket covering sterile sheath 106 where risk of puncture by the needle during insertion is highest. In a preferred embodiment, top enlarged sheath puncture-protecting area 302 and bottom enlarged sheath puncture-protecting area 304 extend at least one-fourth (¼) of an inch beyond the needle-grasping member. In a most preferred embodiment of the present invention, top enlarged sheath puncture-protecting area 302 extends at least threeeighths (⅜) of an inch beyond the needle-grasping member 140.

Figure 4:
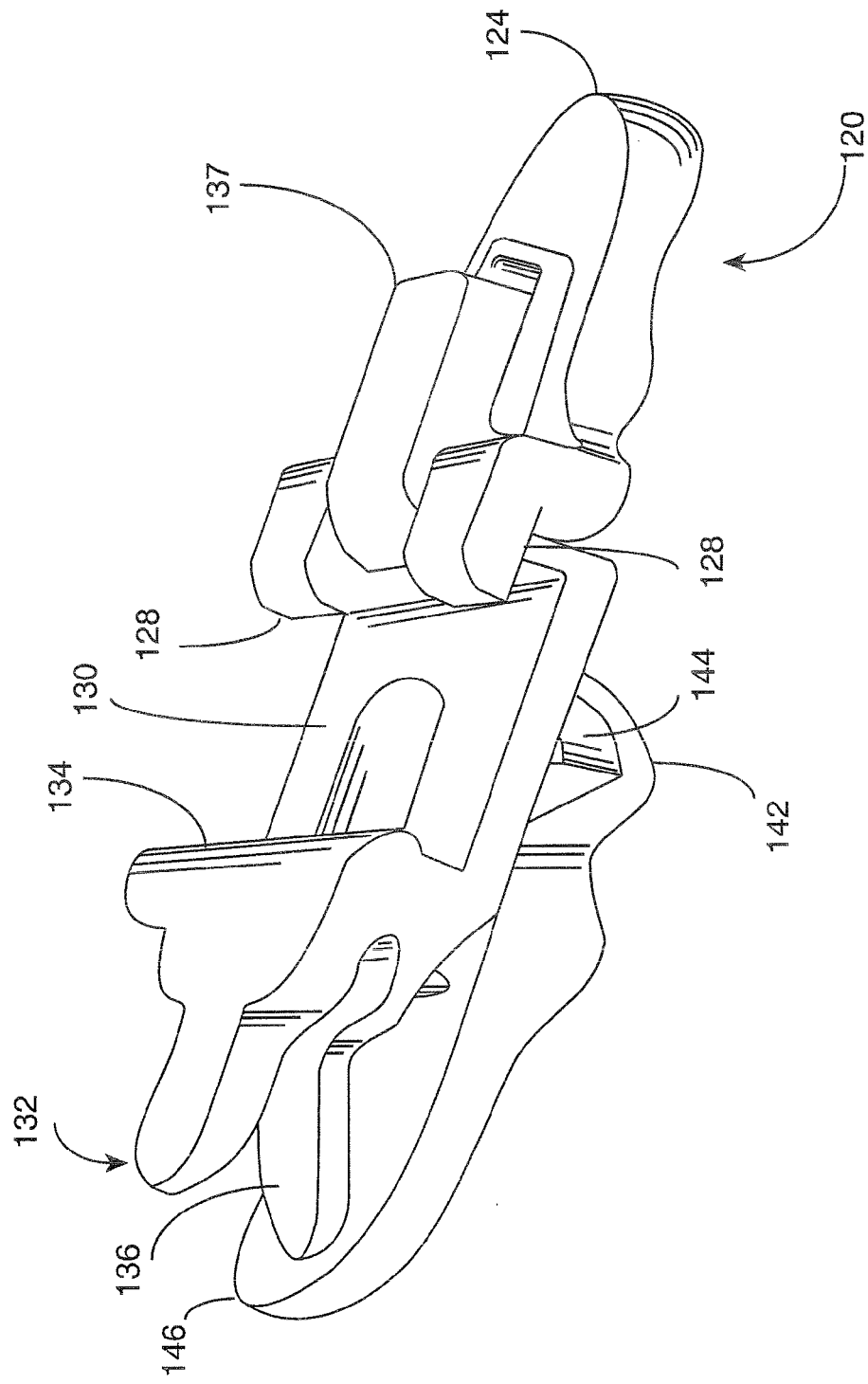
FIG. 4 is a perspective view of the reverse side of the needle guide of FIG. 1.

FIG. 4 is a perspective view of the reverse side of the needle guide of FIG. 1, in a closed and locked position.

Figure 5:
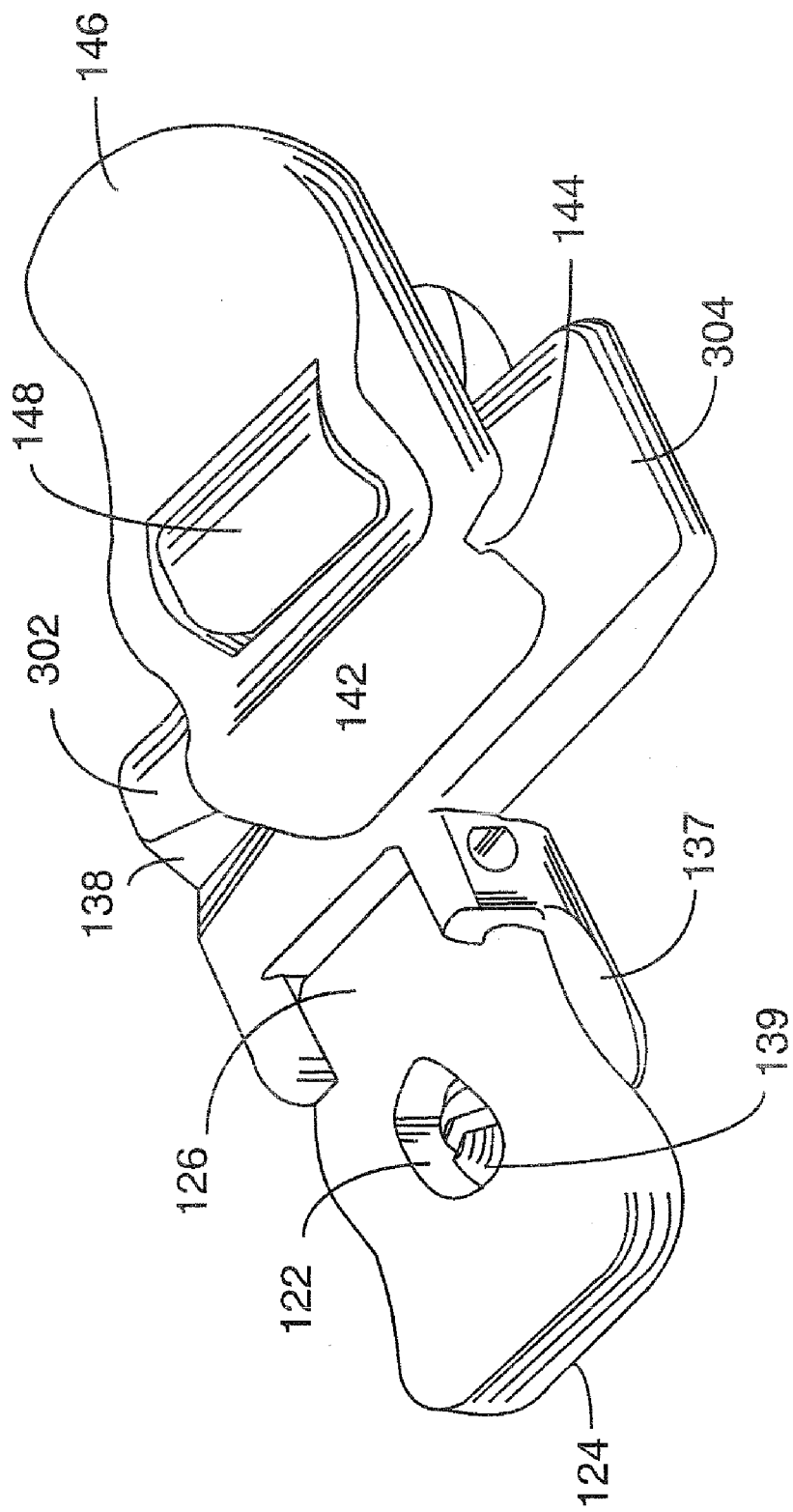
FIG. 5 is a perspective view of an alternate embodiment of the needle guide of the present invention, which is configured to mate with a bracket different from the bracket depicted in FIG. 1.

FIG. 5 is a perspective view of an alternate embodiment of the present invention where the components labeled the same as in FIGS. 1-4 are similar in function, but have differing shape and orientation.

Figure 6:
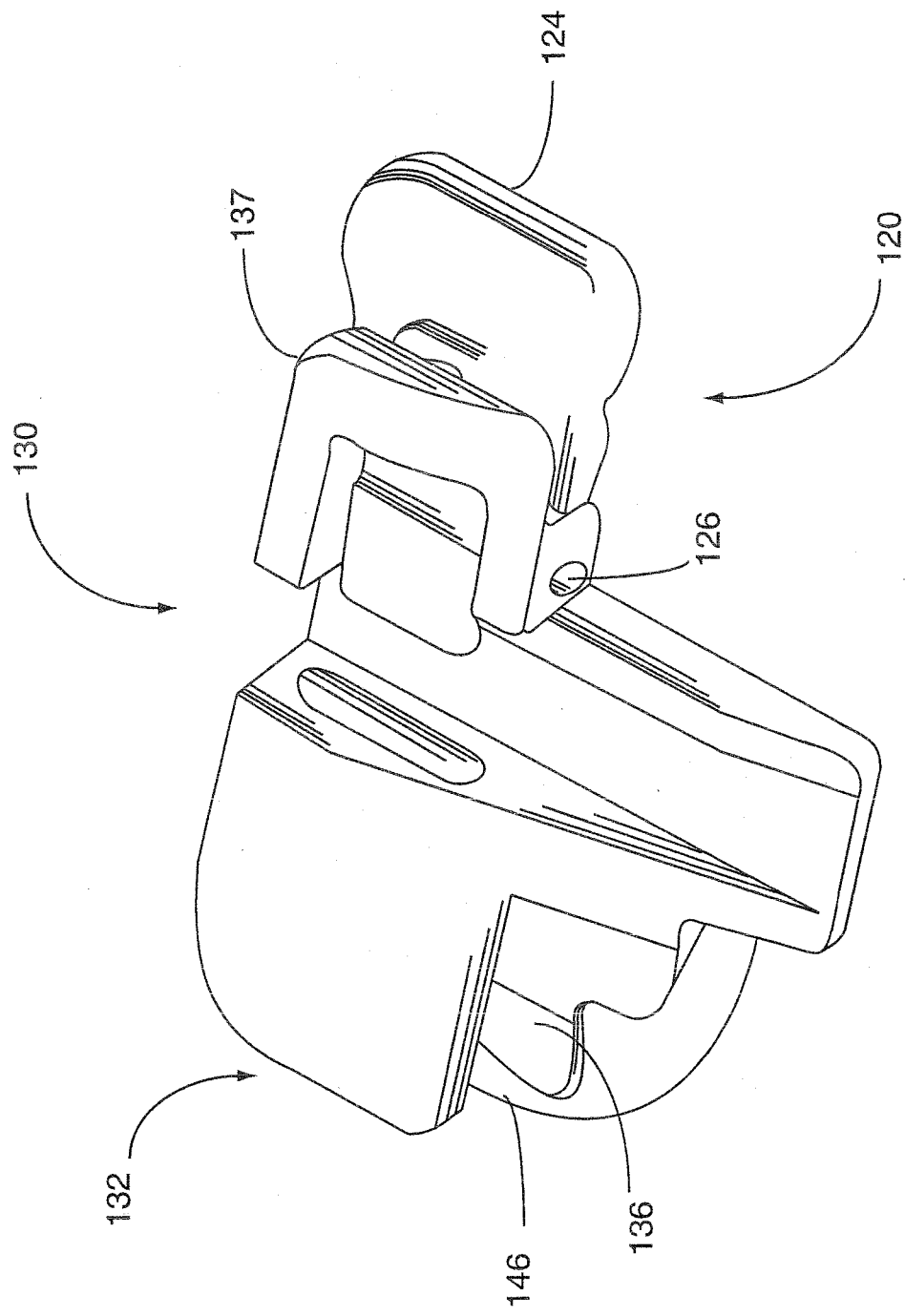
FIG. 6 is a perspective view of a reverse side of the needle guide of FIG. 5.

FIG. 6 is a reverse side of the needle guide of FIG. 5, which is obtained by rotating the device of FIG. 5 so that the opposite side of needle-grasping member handle end 146 is found on the left side of the drawing.

In operation, the apparatus and method of the present invention as described and shown in FIGS. 1-3, could function as follows:

A transceiver bracket 104 is mounted on a medical imaging transceiver 102. A transceiver/bracket covering sterile sheath 106 is pulled over the medical imaging transceiver 102 and transceiver bracket 104 combination. Stationary base portion 130 is mated with transceiver bracket 104 by first engaging stationary base bracket mating portion 134 with transceiver bracket 104, and then movable base handle end 124 is pivoted so that movable base bracket grasping surface 128 contacts the sheathed transceiver bracket 104, and stationary lock end 137 is disposed adjacent the movable base handle end 124. Bullet-nose lock male member 139 is thereby inserted into bullet-nose receiving hole 122 and mates with bullet-nose removal inhibitor surface 123. A needle is placed against top enlarged sheath puncture-protecting area 302 and moved into stationary base needle entrance-guiding channel 138, where it is readily guided into needle-receiving void 144. The needle exits needle-receiving void 144, traverses bottom enlarged sheath puncture-protecting area 304, and is then available for interaction with a patient. Once the procedure is finished, the needle can be removed by pressing needle-grasping member handle end 146, which causes needle-grasping end 142 to move from stationary base portion 130, thereby permitting disengagement of the needle from the needle guide assembly 110.

Figure 7:
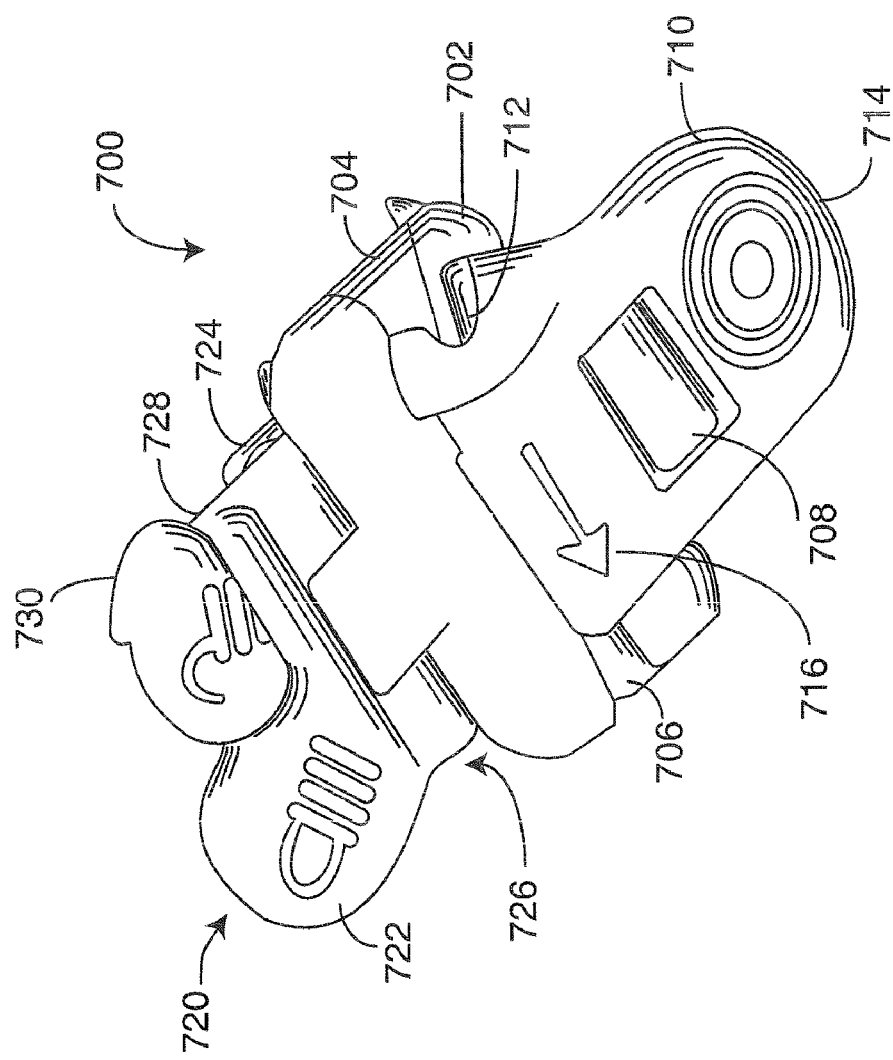
FIG. 7 is a perspective view of the double push-button needle guide of the present invention.
Figure 8:
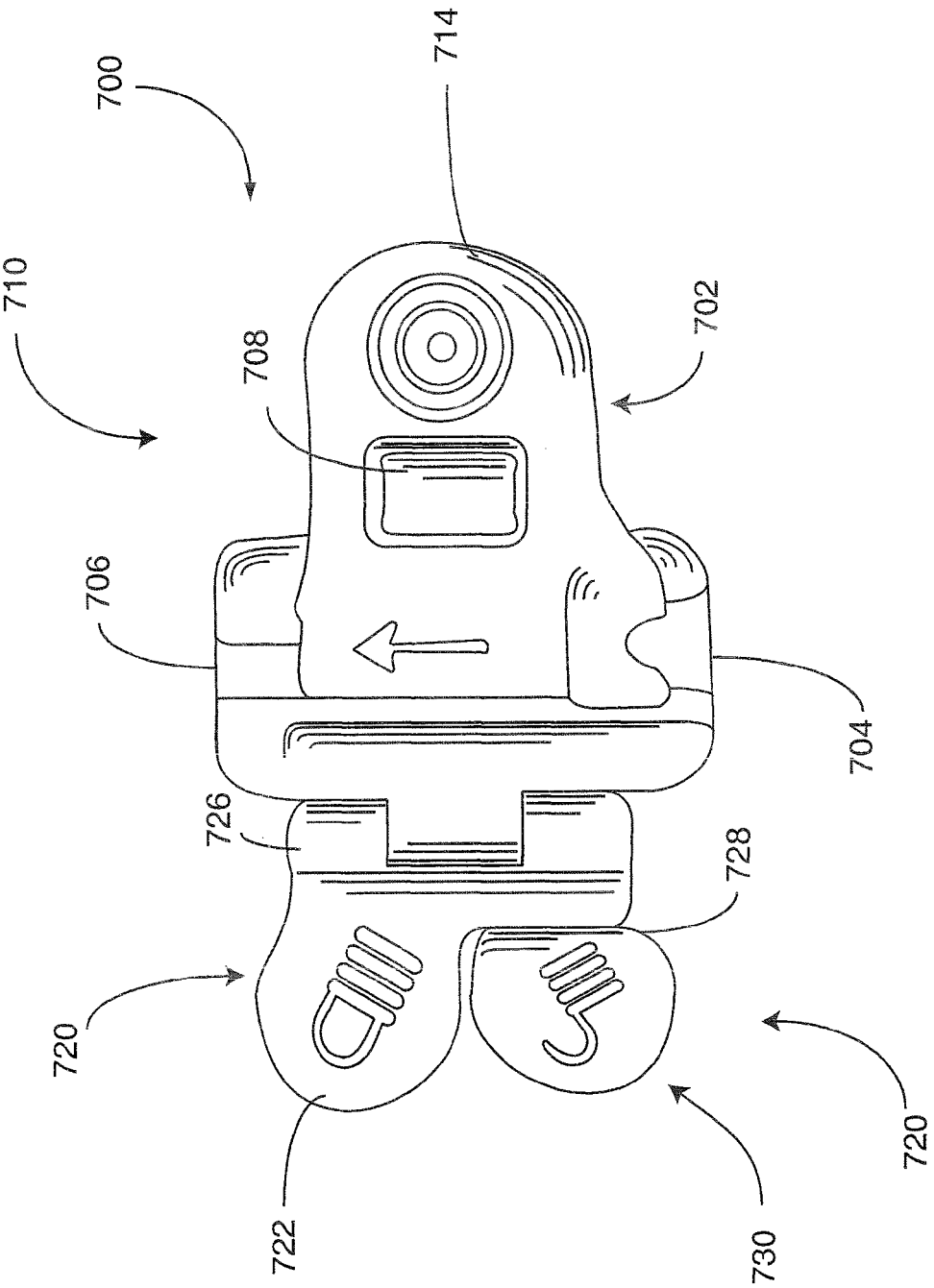
FIG. 8 is a top view of the double push-button needle guide of FIG. 7.

Now referring to FIGS. 7 and 8, there is shown a needle guide 700, in a locked configuration, having a needle guide base portion 702 which mates with a medical imaging transceiver or transceiver bracket (not shown). The transceiver bracket may be similar to the bracket shown in FIG. 1, which has a lip or enlarged end. Needle guide base portion 702 includes a base portion needle funneling area 704, which is a widened area of base portion needle slot 706 for aiding in the insertion of a needle into base portion needle slot 706. Needle guide base portion 702 includes a base portion clamp pivoting area 708, which may act as a fulcrum for needle guide clamping lever 710. Needle guide clamping lever 710 may also include a clamping lever needle funneling area 712 and a clamping lever handle end 714. Clamping lever needle retaining portion 716 may be a cover or retainer over a portion of a needle disposed in base portion needle slot 706. Needle guide base portion 702 is coupled to the medical imaging system transceiver via pivoting locking mechanism 720, which includes a locking button 722 and pivoting locking mechanism grasping member 724. When locking button 722 is pushed inward toward the medical imaging transceiver pivoting locking mechanism grasping member 724, it pivots into place and locks the needle guide 700 with the medical imaging transceiver. Pressing or sliding outwardly and downwardly unlocking button 730 causes locking button 722 and the latch lip 728 to be released and be free to pivot forward and thereby unlocks the needle guide from the transceiver. There is shown a pivoting locking mechanism pivoting area 726.

Unlocking button 730 is preferably a resilient material, so that it can be bent out of the way as pivoting locking mechanism 720 is pushed into the locked position. In a preferred embodiment, all of the components of the needle guide 700 are made of the same plastic material. However, it should be understood that in certain uses, such as for a reusable needle guide, other materials, such as surgical steel, could be used as well. If a non-resilient material is used for unlocking button 730 and unlocking button lever arm 902, then it would be necessary to permit pivoting of unlocking button lever arm 902 and/or unlocking button 730 so as to allow the latching to occur. Similarly, needle guide clamping lever 710 could be resilient, or it could be rigid and pivot with a spring or other biasing mechanism to keep the needle in place. It should be understood that the needle retaining portion of the present invention is merely representative of the many types of needle retaining devices that could be used with the innovative dual locking button approach of the present invention.

Figure 9:
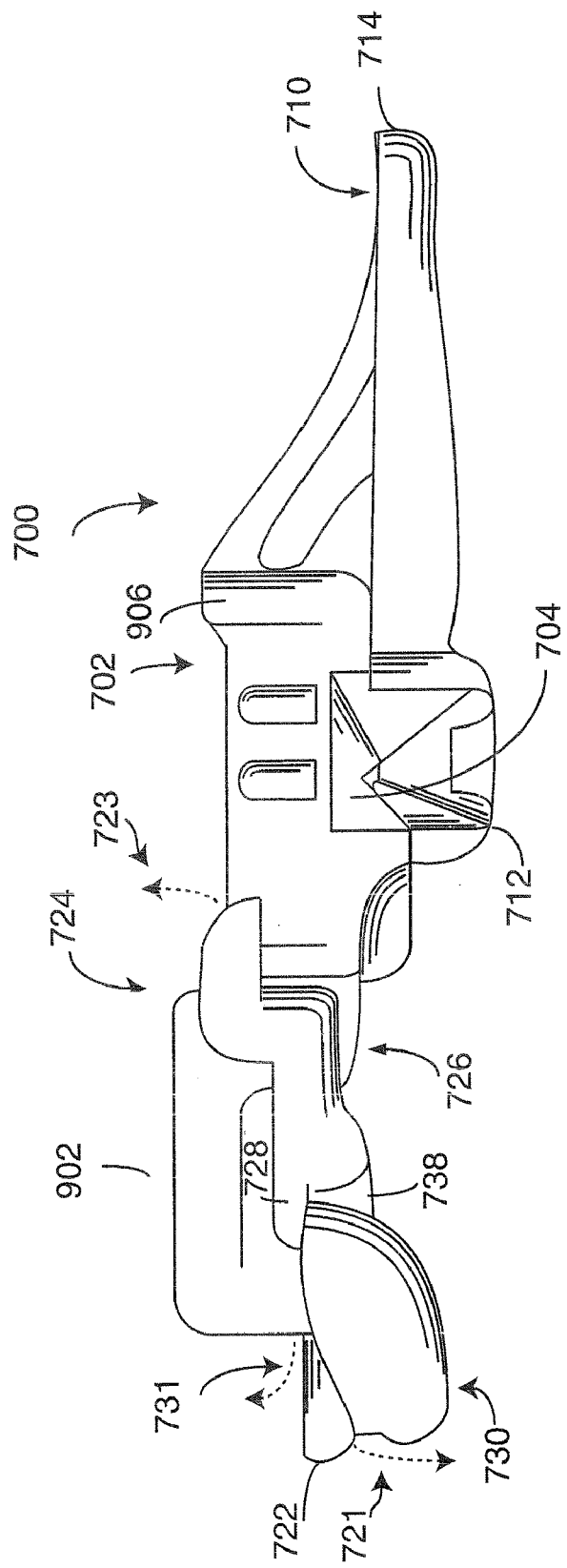
FIG. 9 is a side view of the double push-button needle guide of FIGS. 7 and 8.

Now referring to FIG. 9, there is shown the needle guide 700, in a locked position, from a side view. This side view exposes some of the structure which performs the locking and unlocking functions of pivoting locking mechanism 720 and unlocking button 730 respectively. Unlocking button lever arm 902 is shown such that when unlocking button 730 is pressed or pivoted, along dotted line 731, away from latch lip 728, it causes pivoting locking mechanism 720 to be released and be free to push away or rotate locking button 722 along dotted line 721 into an unlocked position. The position is an unlocked position because when locking button 722 rotates on dotted line 721, pivoting locking mechanism grasping member 724 also pivots away, along dotted line 723, from engagement with the transceiver bracket, thereby unlocking the needle guide from the transceiver bracket. Needle guide base locking side wall and pivoting locking mechanism grasping member 724 together help retain the needle guide base portion 702 in place with the transceiver, which has a portion disposed in the area between needle guide base locking side wall and needle guide base opposing wall 906.

In operation, the needle guide of FIGS. 7-9 could function as follows:

Needle guide 700 is placed over a transceiver bracket with an enlarged end lip. A sterile sheath may be used, or it may be omitted. The needle guide 700 may be disposable, or it may be reusable. Needle guide base portion 702 is slipped over the enlarged lip end of the transceiver bracket, so that needle guide base opposing wall 906 and needle guide base locking side wall surround the enlarged lip end. When needle guide base portion 702 is placed on the bracket, pivoting locking mechanism 720 is initially in an unlocked and forward position and is not engaged by unlocking button 730 at the latch lip 728. Pivoting locking mechanism 720 is then pressed or rotated, so that locking button 722 moves closer to unlocking button 730. Latch lip 728 eventually engages latch end 738 of unlocking button 730. As locking button 722 is rotated further backward, unlocking button 730 pivots backward as well. Once latch lip 728 passes latch end 738 of unlocking button 730, unlocking button 730, which is resilient, springs forward and latches pivoting locking mechanism 720 in a locked position. To unlock the needle guide, unlocking button 730 is pushed along dotted line 731, so that latch end 738 of unlocking button 730 clears latch lip 728 of pivoting locking mechanism 720. Once this occurs, pivoting locking mechanism 720 is free to pivot to an unlocked position, so that locking button 722 pivots along dotted line 721 and pivoting locking mechanism grasping member 724 pivots along dotted line 723.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle, canula or other elongated member. Also, throughout this description, the needle guide is suggested to mate with a transceiver bracket, which is a very common practice of needle guides. However, it is possible, and the present invention is intended to include, mating the needle guide directly to the transceiver, which may or may not have an integrated mounting section formed thereon.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

The invention claimed is:

1. A needle guide assembly comprising:
   a stationary base portion configured to be coupled to a transceiver;
   a needle retaining member which is configured to retain a needle;
   a locking member which is configured to pivot so as to couple said stationary base portion to the transceiver;
   an unlocking button which mates with said locking member and holds said locking member in a pivoted state after said locking member has been pivoted; and,
   said unlocking button further configured to permit release of said locking member, thereby allowing said stationary base portion to be decoupled from said transceiver.

2. A needle guide assembly of claim 1 wherein said locking member comprises a lip portion which engages said unlocking button when said locking member is pivoted beyond a point where said stationary base portion is coupled to said transceiver.

3. A needle guide assembly of claim 2 wherein said unlocking button is configured to pivot away from said lip portion so as to release said lip portion from engagement by said unlocking button.

4. A needle guide assembly of claim 1 wherein:
   said locking member is configured such that a pivoting motion of said locking member in a first predetermined direction results in a coupling of said stationary base portion with a transceiver bracket disposed on said transceiver and further results in a latching engagement with said unlocking button such that said unlocking button holds said locking member in a configuration such that said stationary base portion remains coupled to said transceiver bracket;
   said unlocking button is configured such that a pivoting motion of said unlocking button in a second predetermined direction results in a release of engagement between said unlocking button and said locking member; and,
   said first predetermined direction and said second predetermined direction are substantially the same direction.

5. A needle guide for coupling with a medical imaging transceiver, the needle guide comprising:
   a needle guide base portion, comprising a needle guide base opposing wall, a needle guide base locking side wall;
   a needle retaining device;
   a pivoting locking mechanism comprising a pivoting locking mechanism grasping member and a latch lip;
   said needle guide base portion further comprising an unlocking button lever arm and an unlocking button disposed thereon; said unlocking button and said unlocking button lever arm are configured to flexibly pivot with respect to said needle guide base portion; and, said pivoting locking mechanism configured to rotate about a portion of said unlocking button lever arm; and
said latch lip configured to mate with a latch end of said unlocking button.

6. A needle guide of claim 5 wherein said pivoting locking mechanism pivots in a first direction to couple said needle guide base portion to said medical imaging transceiver; and said unlocking button lever arm pivots in said first direction to unlatch said pivoting locking mechanism from an orientation where said needle guide base portion is coupled to said medical imaging transceiver.

7. A needle guide of claim 6 wherein said unlocking button lever arm is a resilient member.

8. A needle guide of claim 7 wherein said latch lip abuts with said latch end.

9. A needle guide assembly comprising:
a base portion configured to cooperate with a transceiver;
a needle retaining member which is configured to retain a needle;
a locking member which is configured to pivot so as to cooperate with said base portion to the transceiver;
an unlocking member which cooperates with said locking member and holds said locking member in a pivoted state after said locking member has been pivoted;
said unlocking member further configured to permit release of said locking member, thereby allowing said base portion to be decoupled from said transceiver;
wherein said locking member comprises a lip portion which engages said unlocking member when said locking member is pivoted beyond a point where said base portion is coupled to said transceiver;
wherein said unlocking member is configured to pivot away from said lip portion so as to release said lip portion from engagement by said unlocking member;
said locking member configured such that a pivoting motion of said locking member in a first predetermined direction results in a coupling of said base portion with a transceiver bracket disposed on said transceiver and further results in a latching engagement with said unlocking member such that said unlocking member holds said locking member in a configuration such that said stationary base portion remains coupled to said transceiver bracket;
said unlocking member is configured such that a pivoting motion of said unlocking member in a second predetermined direction results in a release of engagement between said unlocking member and said locking member; and,
said first predetermined direction and said second predetermined direction are substantially the same direction.

10. A needle guide assembly comprising:
a stationary base portion configured to cooperate with a transmitter;
a needle retaining member which is configured to retain a needle;
a locking button which is configured to move so as to cooperate with said base portion to the transmitter;
an unlocking button which cooperates with said locking button and holds said locking button in a perturbed state after said locking button has been moved;
said unlocking button further configured to permit release of said locking button, thereby allowing said base portion to be decoupled from said transmitter;
wherein said locking button comprises a lip portion which engages said unlocking button when said locking button is pivoted beyond a point where said base portion is coupled to said transmitter;
wherein said unlocking button is configured to pivot away from said lip portion so as to release said lip portion from engagement by said unlocking button;
said locking button configured such that a pivoting motion of said locking button in a first predetermined direction results in a coupling of said base portion with a transmitter bracket disposed on said transmitter and further results in a latching engagement with said unlocking button such that said unlocking button holds said locking button in a configuration such that said stationary base portion remains coupled to said transmitter bracket;
said unlocking button is configured such that a pivoting motion of said unlocking button in a second predetermined direction results in a release of engagement between said unlocking button and said locking button; and,
said first predetermined direction and said second predetermined direction are substantially the same direction.

* * * * *